United States Patent
Maurice

(10) Patent No.: US 6,858,025 B2
(45) Date of Patent: Feb. 22, 2005

(54) CRYO-SURGICAL APPARATUS AND METHOD OF USE

(75) Inventor: George T. Maurice, North Falmouth, MA (US)

(73) Assignee: Medically Advanced Designs, LLC, Cumming, GA (US)

(*) Notice: Subject to any disclaimer, the term of this patent is extended or adjusted under 35 U.S.C. 154(b) by 0 days.

(21) Appl. No.: 10/213,568

(22) Filed: Aug. 6, 2002

(65) Prior Publication Data

US 2004/0215178 A1 Oct. 28, 2004

(51) Int. Cl.[7] ............................................. A61B 18/18
(52) U.S. Cl. ........................... 606/21; 606/22; 606/23; 606/41; 128/898
(58) Field of Search .................. 606/20–26, 41; 128/898

(56) References Cited

U.S. PATENT DOCUMENTS

| | | |
|---|---|---|
| 4,015,606 A | 4/1977 | Mitchiner et al. |
| 4,946,460 A | 8/1990 | Merry et al. |
| 5,800,487 A | 9/1998 | Mikus et al. |
| 5,899,897 A | 5/1999 | Rabin et al. |
| 5,906,612 A | 5/1999 | Chinn |
| 6,074,412 A | 6/2000 | Mikus et al. |
| 6,190,378 B1 | 2/2001 | Jarvinen |
| 6,305,378 B1 * | 10/2001 | Lesh ............................ 128/898 |
| 6,379,348 B1 | 4/2002 | Onik |
| 6,648,880 B2 * | 11/2003 | Chauvet et al. ............... 606/21 |

OTHER PUBLICATIONS

Rubinsky, Boris, "Cryosurgery," *Annu. Rev. Biomed. Eng.* 2:157–187 (2000).

* cited by examiner

*Primary Examiner*—Rosiland Rollins
(74) *Attorney, Agent, or Firm*—Klarquist Sparkman, LLP

(57) ABSTRACT

Cryosurgical apparatus includes an elongate cryoprobe having a cooling portion and an electrically conductive first portion in the region of the cooling portion. A removable sheath having an electrically conductive second portion is received on the cryoprobe with its electrically conductive second portion spaced from the electrically conductive first portion of the cryoprobe. Electrical insulation is interposed between the first portion and the second portion. Coolant material supplied to the cryoprobe produces tissue freezing in the region of the cooling portion. Electromagnetic energy supplied to either the first portion or the second portion, while the other of such first portion or second portion is connected to ground, provides selective heating in tissue surrounding an iceball produced by the cooling portion to control the configuration of the iceball.

39 Claims, 3 Drawing Sheets

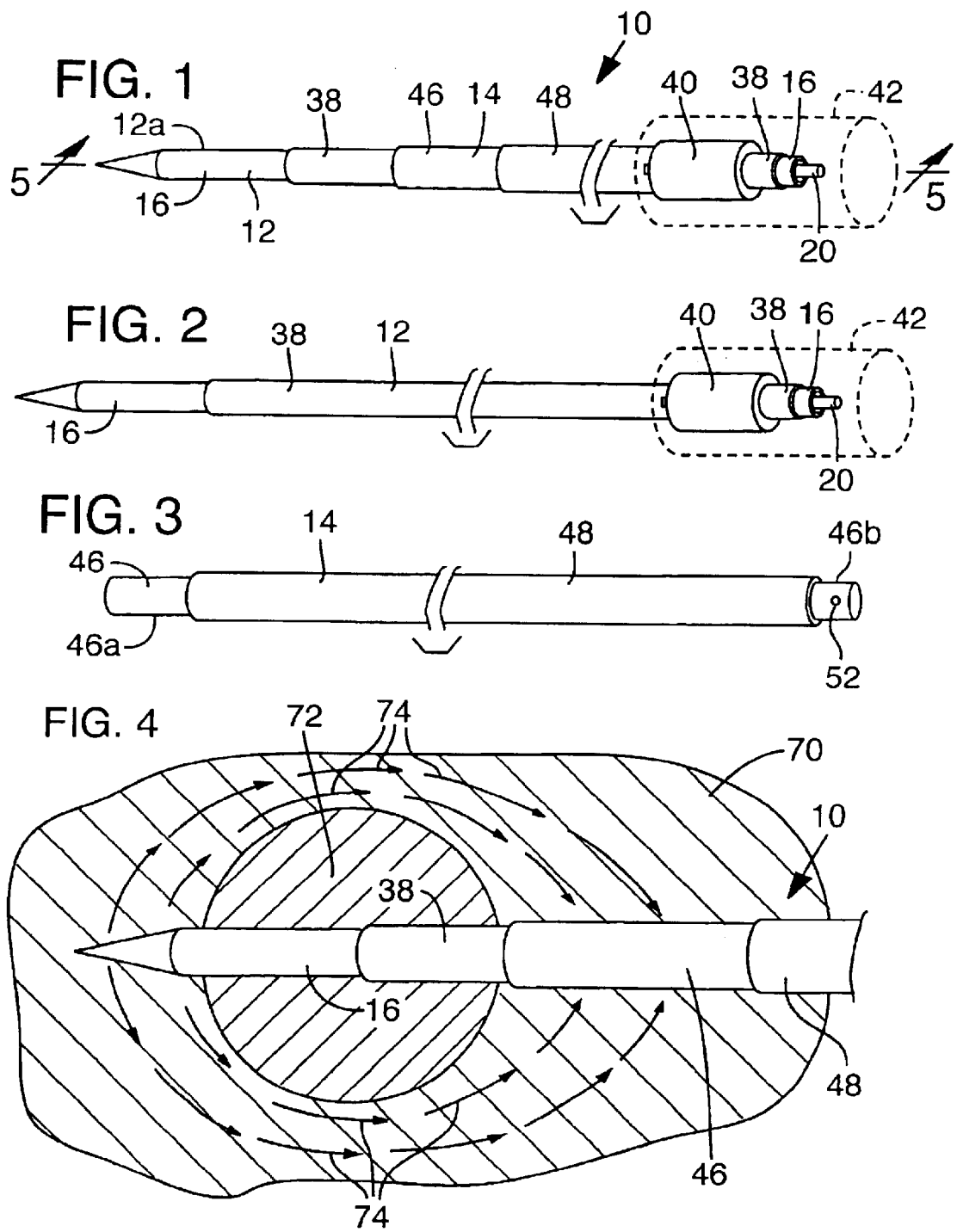

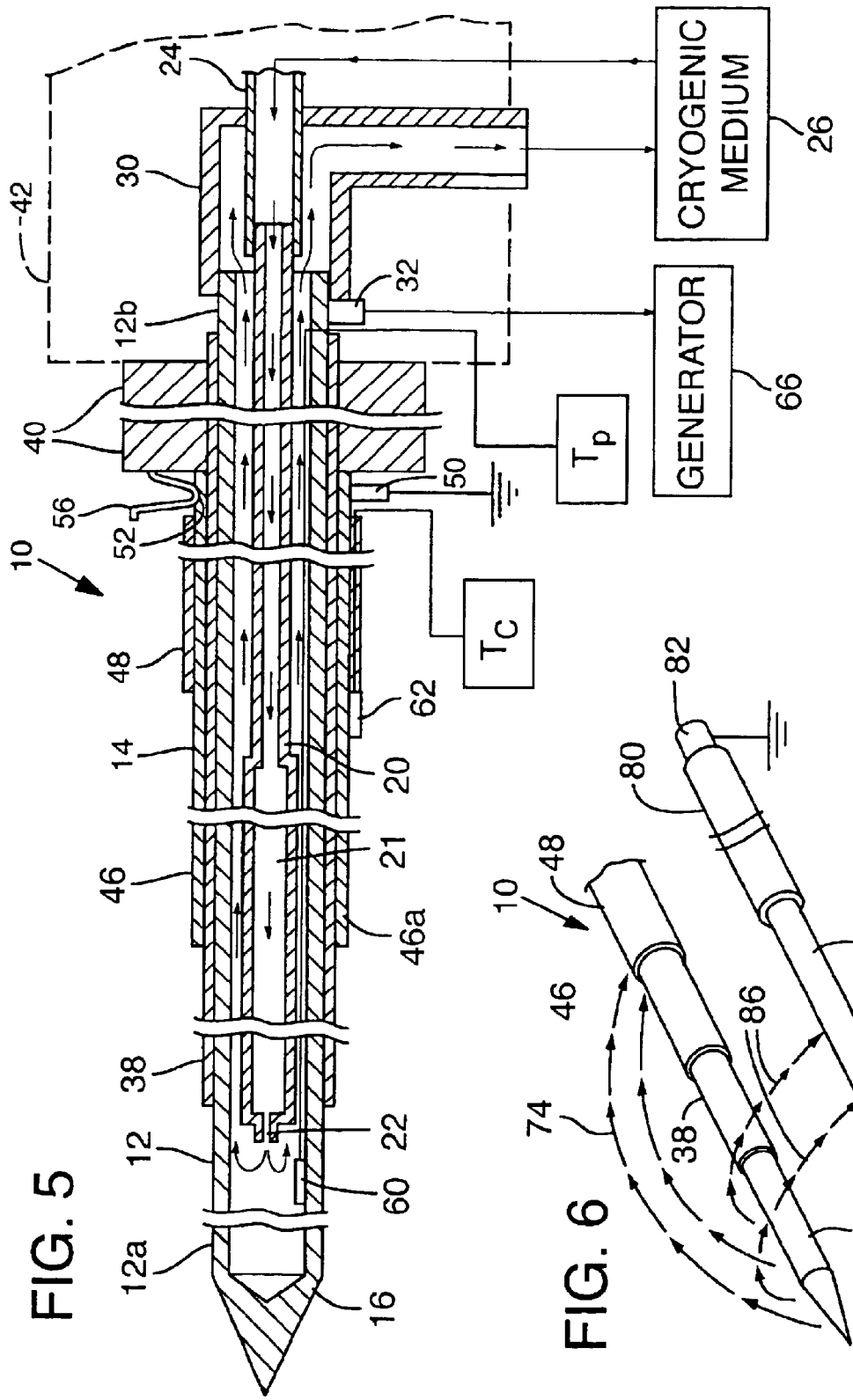

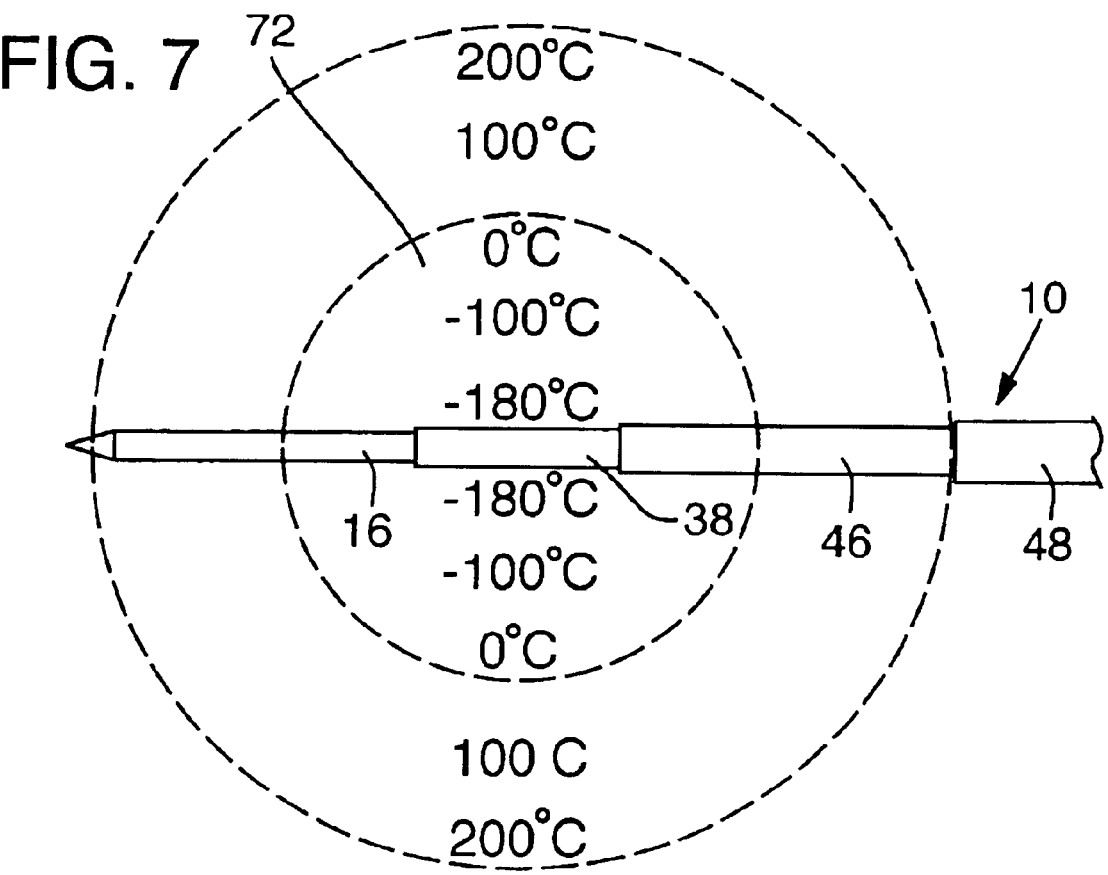
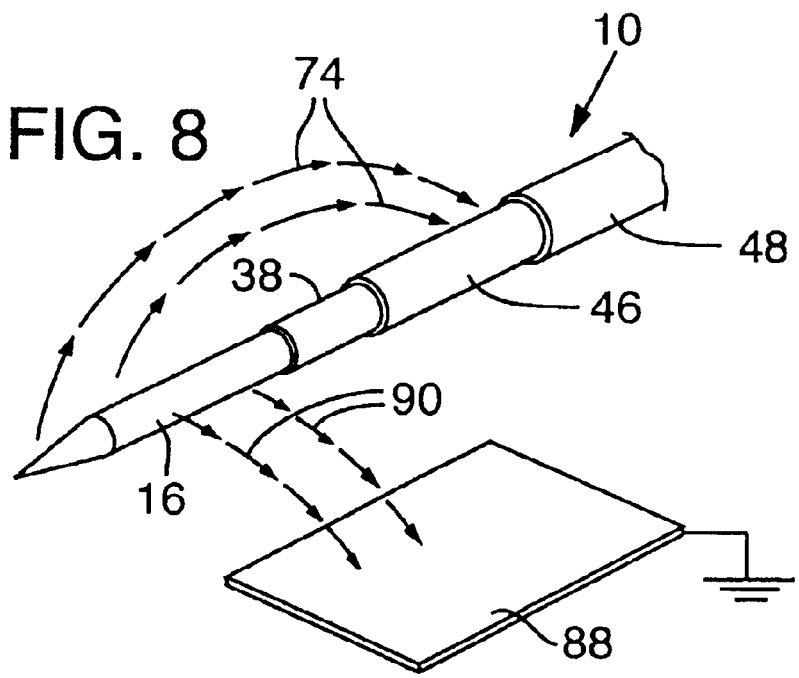

CRYO-SURGICAL APPARATUS AND METHOD OF USE

FIELD

This invention relates to cryoprobe apparatus for use in cryosurgery and other applications. More specifically it relates to a cryo-surgical apparatus having the enhanced ability to control the configuration of iceballs formed in tissue.

BACKGROUND

Cryosurgery, or cryoablation, is one of the oldest of the local thermal ablation techniques. It was initially developed in the 19$^{th}$ century. It has been used for destroying and controlling tissue, such as tumors, deep within the body.

The use of cryosurgical probes for cryosurgery, or cryoablation, has been described in many clinical reports for the treatment of a variety of different benign and malignant tumors. In addition the use of the cryosurgical probes for cryosurgery, or cryoablation, has been described in laparscopic and percutaneous clinical reports.

A summary of the general history of cryosurgery and the mechanism involved therein is well set out in an article entitled "Cryosurgery," by Boris Rubinsky published in the *Annual Reviews in Biomedical Engineering*, 2000, 2:157–187, which is incorporated herein by reference.

Cryosurgery, or cryoablation, is a method of in situ freezing of tissues in which subfreezing temperatures are delivered through penetrating, or surface, cryoprobes in which a cryogen, or coolant agent or material, is circulated. The cryosurgical probe quickly freezes tissue adjacent the cryoprobe in order to cause cryonecrosis or tissue death. Irreversible tissue destruction generally occurs at temperatures below −20° C. and cell death is caused by direct freezing, cell membrane rupture, cell dehydration, denaturation of cellular proteins, and ischemic hypoxia. The necrotic tissue then is absorbed or expelled by the body. Multiple applications of freezing and thawing may be applied before the cryoprobes are removed.

This method of cryosurgery has a number of fundamental drawbacks. Presently, cryosurgery, or cryoablation, is primarily an open surgical technique. Depending on the tumor size, one to eight cryoprobes, ranging in diameter from 1.5–8 millimeters in size, are placed in the target tissue. A cryogenic material, typically liquid nitrogen or argon gas, is circulated through the cryoprobes for several minutes in order to achieve temperatures below −120° C. After a second freeze, the cryoprobes are heated, typically by circulating warming fluid or helium gas, and removed and the tracts are packed for hemostasis. Bleeding is often a common complication reported after the cryoablative or cryosurgical procedure. Additional complications include fever, renal failure, sepsis, disseminated intravascular coagulation, and leukocytosis. Other limiting factors include large cryoprobe sizes, damage to the tissue directly adjacent to the cryozone or iceball, and the size and the shape of the iceballs formed in the tissue.

For example, the use of cryosurgical probes for the use in cryosurgery or ryoablation of the prostate described in Onik and Cohen, "Transrectal Ultrasound Percutaneous Radial Cryosurgical Ablation of the Prostate," *Cancer* 72:1291, 1993, details the cryosurgical or cryoablative procedure. The cryocoolers or cryoprobes are placed into the prostate gland through cannulas that were previously placed using ultrasound guidance. The irregular shape of the enlarged prostate gland requires a specific iceball shape in order to treat the tissue completely. In order to prevent neighboring tissues or structures from being damaged, the urethra, external sphincter, and the bladder neck sphincter are protected from freezing by a continuous infusion of warm saline through a catheter placed in the urethra. Additionally, cryosurgery or cryoablation of hepatic metastasis poses a different challenge. Unlike primary hepatic tumors, for example hepatocellular carcinoma, the shapes of hepatic metastasis are irregular and typically are in poor locations whereby adjacent tissue or structure damage is a major concern.

The aforementioned difficulties in treating a variety of different benign or malignant tissues and the complications associated with current cryosurgical probes and cryoablative procedures has brought about the need for improved cryo-surgical devices and methods.

SUMMARY

Disclosed is a cryosurgical apparatus and methods of use capable of providing control over the configuration of the iceball formed in tissue.

In one embodiment, an elongate cryoprobe has a cooling portion and an electrically conductive first portion in the region of the cooling portion, an energy conducting element is positioned adjacent the cryoprobe and has an electrically conductive second portion in a region spaced from the first portion on the cryoprobe, and a source of electromagnetic energy is operatively connected to one of the first and second portions operable to produce heating of tissue in the region of the iceball to control configuration of the iceball.

In an embodiment, the apparatus and method are such that electromagnetic energy is transmitted through the tissue surrounding the iceball formed by the cooling portion of the cryoprobe with such energy heating the adjacent and surrounding tissue to assist in controlling the configuration of the iceball.

In some embodiments, the apparatus and/or method is capable of either protecting adjacent tissue or structure from thermal damage through selective heating of surrounding tissue, or may induce additional thermal damage to surrounding tissue by means of heat producing energy transmission.

In some embodiments of the invention, apparatus and/or method is provided for controlling the total amount of energy imposed in the adjacent tissue from both the thermal energy produced by the freezing mechanism or the electromagnetic power source energy, thus impacting the total amount of tissue death, or tissue necrosis.

BRIEF DESCRIPTION OF THE DRAWINGS

FIG. 1 is a perspective view of a portion of apparatus according to one embodiment of the invention with an elongate centrally positioned cryoprobe surrounded by a sheath;

FIG. 2 is a view of the cryoprobe similar to FIG. 1 with the sheath removed;

FIG. 3 is a perspective view of the sheath removed from the cryoprobe;

FIG. 4 is an enlarged perspective view of the distal end portion of the cryoprobe apparatus inserted in tissue and operating to form a selectively configured iceball;

FIG. 5 is an enlarged cross-sectional view taken generally along the line 5—5 in FIG. 1;

FIG. 6 is a distal end perspective view of another embodiment of the invention;

FIG. 7 is an enlarged perspective view of the distal end portion of the cryoprobe apparatus that depicts an example of an operational thermal range; and FIG. 8 is a distal end perspective of another embodiment of the invention.

DETAILED DESCRIPTION

The singular forms "a," "an," and "the" refer to one or more than one, unless the context clearly dictates otherwise. For example, the term "comprising a cryoprobe" includes single or plural cryoprobe and is considered equivalent to the phrase "comprising at least one cryoprobe."The term "or" refers to a single element of stated alternative elements or a combination of two or more elements. For example, the phrase "radiofrequency or microwave energy" refers to radiofrequency energy, microwave energy, or both radiofrequency and microwave energies.

The term "comprises" means "includes." Thus, "comprising A and B" means "including A and B," without excluding additional elements.

The term "proximal" refers to a portion of an instrument closer to an operator, while "distal" refers to a portion of the instrument farther away from the operator.

The term "subject" refers to both human and animal subjects. In certain embodiments, the subject is a human or other mammal.

Referring to the drawings, and more specifically to FIGS. 1–3 and 5, at 10 is indicated generally an apparatus according to an embodiment of the invention. The apparatus includes an elongate cryoprobe 12 and a surrounding coaxially disposed sheath, or cannula, 14. The cryoprobe has a distal end 12a, and a proximal end 12b nearest the operator.

The cryoprobe includes an elongate hollow needle member 16 which is closed and pointed at its distal end and is open at its proximal end. An elongate coaxially disposed inner tube 20 is mounted within member 16. As seen in FIG. 5, tube 20, comprising a Giaque-Hampson heat exchanger 21 and a Joule-Thomson nozzle 22, ends toward the closed distal end of member 16 and extends outwardly from the proximal end of member 16. Tube 20 provides a cryogenic medium supply channel through which coolant, or refrigerant material, may be supplied to cryoprobe 12. A space provided between the outside of tube 20 and the inner walls of member 16 provide a return path for cryogenic medium to exit through the proximal end of member 16.

As best seen in FIG. 5, a tubing connector, such as that indicated generally at 24, may be operatively connected to the proximal end of tube 20 through which the cryogenic medium may be supplied from a cryogenic medium supply indicated generally at 26. A return connector 30 operatively connected to the proximal end of member 16 provides a return path for the cryogenic medium to return to the cryogenic medium supply 26 or to another region to which to it is desired to direct spent coolant fluid.

As indicated by the arrows in FIG. 5, cryogenic medium from cryogenic supply 26 is directed through tube 20, comprising a Giaque-Hampson heat exchanger 21 and a Joule-Thomson nozzle 22, toward the distal end of cryoprobe 12, exiting the Joule-Thomson nozzle 22 toward the distal end portion of member 16 which serves as an expansion chamber and cools toward the distal end 12a of the cryoprobe. Fluid then returns along the channel provided between tube 20 and the member 16 to exit the apparatus through return connector 30.

The member 16 is constructed of a thermally conductive material such that the distal end portion of member 16 serves as what may be considered a freezing tip, or cooling portion, which upon activation may freeze tissue in which it is inserted.

Further member 16 may be constructed of an electrically conductive material, such as surgical steel, and has an electrical connector 32 coupled to its proximal end as illustrated in FIG. 5. This allows it to be operatively connected to electrical or electromagnetic equipment, as will be described further below and to conduct electrical or electromagnetic energy between its proximal end and its distal end.

Although member 16 is described herein as being constructed generally of electrically conductive material throughout, such that energy may be conducted between its proximal end and its distal end, it should be recognized that portions of member 16 may be made of non-electrically conductive material and that only a portion adjacent the cooling portion of the cryoprobe, would have an electrically conductive exposed portion. In such case appropriate conductors would extend between the electrically conductive portion on the member and the electrical connector 32 such that electrical energy could be transmitted therebetween.

A layer of electrical insulating material 38 covers the major portion of member 16 between its proximal and distal ends. As best seen in FIG. 5, the proximal end 12b of member 16 may be left somewhat exposed for the application of connector 32, and the distal end portion of member 16 remains exposed. The electrical insulating material may be a non-conducting rubber, plastic, or other polymer capable of shielding tissue adjacent the insulating material.

A mounting sleeve 40 is secured to a proximal end portion of cryoprobe 12 and serves to have a holder, such as that indicated generally dashed outline at 42, coupled thereto providing a hand hold through which an operator may grasp and manipulate the apparatus during use. Since the holder 42 may take many different forms, it is shown here only in a generalized form.

Referring to FIGS. 3 and 5, sheath 14 comprises an elongate cannula 46 having a distal end 46a and proximal end 46b. The cannula has a central opening, or lumen, sized to slidably receive member 16 and its associated electrical insulating material 38 there through. Cannula 46 has a layer of electrically insulating material 48 covering a major portion thereof. The electrical insulating material covering the cannula may be similar to that used on member 16. The distal and proximal ends of cannula 46 are not covered by insulating material, but are left exposed as best illustrated in FIGS. 3 and 5.

Cannula 46 may be made of an electrically conductive material and has an electrical connector 50 attached to its proximal end, such that electrical energy may be transmitted between the distal end 46a and proximal end 46b of cannula 46. In an alternate construction, the cannula may be made of a non-electrically conductive material with an electrically conductive portion provided at its distal end 46a and appropriate electrical conductors connecting such electrically conducting portion at its distal end to a connector such as that indicated at 50 whereby electrical energy may be transmitted between such points.

A detent 52 is formed in the proximal end portion 46b of cannula 46. A yieldable interlock mechanism 56 secured to mounting sleeve 40 is positioned to releasably engage detent 52 to hold sheath 14 on cryoprobe 12 as illustrated in FIG. 5. The interlock mechanism is spring biased into the holding position illustrated in FIG. 5. The mechanism is easily released by manually urging the interlock mechanism from detent 52 allowing the sheath 14 to be slid off of cryoprobe 12.

The apparatus, as illustrated in FIGS. 1 and 5, has sheath 14 mounted coaxially on cryoprobe 12 and held in place by interlock mechanism 56. In this position electrical insulating material 48 covers the major portion of the length of cannula 46, leaving its distal end portion 46a exposed. Electrical insulating material 38 surrounding a major portion of the length of needle member 16 electrically insulates cannula 46 from member 16. As best seen in FIGS. 1 and 5, electrical insulation material 38 extends longitudinally outwardly from the distal end portion 46a of cannula 46. The distal end of member 16 extends longitudinally outwardly from insulating material 38 and from cannula 46, such that the distal end portion of member 16 is both electrically and thermally exposed.

Although cryoprobe 12 and sheath 14 are shown as having a circular crosssection it should be understood that other cross-sections are acceptable also. These could include oval, rectangular, triangular or others.

Referring to FIG. 5, a temperature sensing thermocouple 60 mounted within cryoprobe 12 is operable to determine the temperature at the distal end portion of the cryoprobe and transmit such information to a registering instrument indicated $T_p$. Similarly, a thermocouple 62 associated with cannula 46 is operable to transmit information regarding temperature in the distal region of the cannula to a temperature registering device indicated at $T_c$.

Referring still to FIG. 5, the needle member 16 and cannula 46 are adapted for connection to apparatus for providing heat energy to tissue in a region adjacent the cryoprobe. In the illustrated embodiment, needle member 16 is connected through electrical connector 32 to an electromagnetic energy generator 66, which in the illustrated embodiment may be a radio frequency (RF) generator, a microwave generator, or other appropriate variable frequency electromagnetic energy generator. Cannula 46 is shown as operatively connected through its electrical connector 50 to electrical ground. In alternate embodiments cannula 46 could be connected to the energy generator and cryoprobe 12 connected to ground.

Commercially available electromagnetic energy generators may be used in the system to produce the desired RF energy, microwave energy, or other appropriate variable frequency electromagnetic energy. Those skilled in the field will be well versed in the types of electromagnetic energy generators which may be appropriate for producing the types and levels of electromagnetic energy required to provide the desired results for controlling the configuration of the iceball produced. The electromagnetic energy supplied to the apparatus can be controlled in either a modulated or pulsed fashion. Similarly, the cryogenic material supply used in the system may be any commercially available cryogenic material supply appropriate for such operation, as are well known to those skilled in the field.

Explaining operation of the apparatus thus far disclosed, and referring initially to FIG. 4, the distal end of apparatus 10 is inserted into tissue 70 of a subject to be treated. The sharpened distal end of needle member 16 facilitates insertion. After the cryoprobe has been inserted to a desired target location within the tissue, a cryogenic medium from cryogenic medium supply 26 is supplied to member 16, such that tissue in the region surrounding and adjacent the cooling portion of the cryoprobe is frozen into an iceball generally as indicated at 72.

After the iceball begins to form electromagnetic energy from generator 66, such as radio frequency or microwave energy or other appropriate variable frequency electromagnetic energy, is supplied to conductive needle element 16 while electrically conductive cannula 46 is connected to ground. Electromagnetic energy transmitted to the distal end of needle member 16 flows from member 16, through tissue 70 surrounding iceball 72 to grounded cannula 46 as illustrated generally by arrows 74 in FIG. 4. The transmission of electromagnetic energy through the tissue adjacent and surrounding the iceball serves to heat such surrounding tissue and control the configuration of the iceball. The extent of control of configuration of the iceball is produced by the level and timing of energy transmitted to needle member 16, through tissue 70 surrounding iceball 72, and to cannula 46.

As is know by those skilled in the art, the propagation of electromagnetic energy through tissue is frequency dependent. The operator will choose an appropriate frequencey to produce the desired control of the configuration and size of the iceball formed.

The cryogenic material preferably will be able to cool tissue to temperatures in a range of about 0° C. to −180° C. or lower.

The electromagnetic energy impressed in the tissue may be capable of causing tissue to be heated to temperatures from 10° C. to 200° C. or more.

Although cooling temperatures to −180° C. and heating temperatures to 200° C. have been noted, it should be recognized that the supply of the cryogenic medium to the cryoprobe may be controlled to produce appropriate freezing temperatures for tissue in the region of the cooling portion of the cryoprobe and the heating temperature for tissue may be controlled by the appropriate supply of electromagnetic energy from generator 66. The cooling temperature used for freezing and the tissue heating temperatures used will be chosen by the operator as most appropriate for the procedure.

FIG. 7 illustrates an example of temperature ranges produced in tissue surrounding the apparatus during use. As seen the temperature gradients in tissue may range from a low of about −180° C. contiguous to the cryogenic portion of the apparatus to a high of about 200° C. spaced a distance therefrom with a range of intermediate temperatures therebetween. The temperature gradients shown here are examples only.

The temperature used for freezing is measured by thermocouple 60 in needle member 16 and is registered on device $T_p$. Similarly, the heating temperature adjacent the apparatus may be judged from the temperature reading from thermocouple 62 on cannula 46 and noted on registering device $T_c$.

As an example only, the cryoprobe 12 generally may be any suitable length and diameter needed for selected procedures. In some embodiments, the cryoprobe may have a length of about 10 cm to 25 cm and a diameter of about 0.1 to 0.8 cm. The noninsulated distal end portion 12a of cryoprobe 12 would project about 2 cm from the outer end of insulating covering 38. Insulating covering 38 would project approximately 0.5 cm longitudinally outwardly from cannula 46 and exposed distal end portion 46a of cannula 46 could extend approximately 2 cm outwardly from its insulating covering 48. These, however, are exemplary dimensions only. The size of components and the portions exposed both for thermal conductivity and electrical conductivity may be altered for different embodiments and to provide selected cooling and heating capabilities.

FIG. 6 illustrates another embodiment in which a second electrically conductive element 80 is used. Electrically conductive element 80 includes an elongate electrically conductive member 82 having a sharpened distal end 82a for insertion into tissue and a covering of electrically nonconductive material 84 covering a major portion of the length of element 80, but leaving the distal end 82a exposed. Member 82 is connected to electrical ground as indicated.

In operation of the apparatus shown in FIG. 6, cryoprobe apparatus 10 is inserted into tissue to be treated as previously described and appropriately connected to the cryogenic medium supply 26, generator 66 and electrical ground. Element 80 is inserted into tissue adjacent and spaced laterally from cryoprobe 12, with the exposed portion of member 82 aligned as desired with the exposed cooling portion and electrically conductive portion of needle member 16.

When energy from generator 66 is transmitted to needle member 16, such energy will flow not only to grounded cannula member 46 as indicated by arrows 74, but also to grounded member 82, as indicated by arrows 86. With member 82, and possibly other similar electrically conductive elements placed adjacent but spaced laterally from the cryoprobe, the electromagnetic energy transmitted through the tissue will serve to further control the configuration of an iceball generated by cryoprobe apparatus 10.

FIG. 8 illustrates another embodiment in which a second electrically conductive element 88, also referred to as a dispersive electrode, is used. Element 88 comprises an electrically conductive plate which is electrically grounded. The plate may be placed against the skin of a subject in which the cryoprobe apparatus is to be used.

In operation of the apparatus shown in FIG. 8, cryoprobe apparatus 10 is inserted into tissue to be treated and appropriately connected to the cryogenic medium supply 26, generator 66, and electrical ground. Element 88 is placed in contact with the skin of a subject to be treated in a region appropriately chosen by the operator. When energy from generator 66 is transmitted to needle member 16 such energy will flow not only to grounded cannula member 46 as indicated by arrows 74, but also to grounded member 88 as indicated by arrows 90. The electromagnetic energy transmitted between needle member 16 and member 88 will serve to further control the configuration of an iceball generated by cryoprobe apparatus 10.

Although the apparatus has been described in the configuration illustrated and as set out above, it should be recognized that other forms could be used also which would function as desired. For example, the cooling portion of the cryoprobe might be disposed intermediate the ends of the apparatus and the exposed conducting element could be disposed toward, or at, the distal end of the apparatus. It is, however, important that electrically insulating material be interposed between the two electrically conductive components (one of which receives electromagnetic energy from the generator and the other of which is connected to ground) such that tissue heating energy will flow through tissue extending about the iceball formed by the cooling portion of the cryoprobe.

The method for producing appropriate freezing and control of the configuration of iceball may be further enhanced by modifying (increasing or decreasing) the electrical and thermal conductivity characteristics of tissue in the region of the cryoprobe, thus impacting the total amount of tissue death or tissue necrosis. This may be accomplished by introducing various agents into the tissue, said agents being selected based on biocompatibility, thermal and electrical properties. Such agents are known by those skilled in the art.

The therapeutic effect of apparatus and method of operation thus far described also may be further enhanced by the injection of elements that have encapsulated agents therein which are released by heat. The injection of such materials into regions of tissue adjacent the cryoprobe apparatus permits heat generated from the electromagnetic energy generators in heating tissue adjacent the iceball to release agents from their encapsulated state to provide additional therapeutics effects.

While preferred embodiments and methods have been described herein, it should be apparent to those skilled in the art that variations and modification as possible without departing from the spirit of the invention as set out in the following claims.

What is claimed is:

1. Cryosurgical apparatus comprising
   an elongate cryoprobe having a proximal end, a distal end,
   a cooling portion adapted to be positioned in tissue to be treated and operative to cool tissue to form an ice ball in such tissue upon activation, and an electrically conductive first portion, an energy conducting element coupled to said cryoprobe and having an electrically conductive second portion in a region spaced from said first portion, electrical insulation interposed between said first portion and said second portion, and a source of electromagnetic energy operatively connected to one of said first portion and second portion operable to produce heating of tissue in the region of said iceball to control the configuration of the iceball.

2. The apparatus of claim 1, wherein said source of energy comprises a radiofrequency energy generator.

3. The apparatus of claim 1, wherein one of said first portion and second portion is operatively connected to said electromagnetic energy generator and the other of said first and second portions is connected to electrical ground.

4. The apparatus of claim 1, wherein said cryoprobe comprises an elongate electrically conductive member, said energy conducting element surrounds a portion of said conductive member, and said electrical insulation is disposed between said conductive member and said energy conducting element.

5. The apparatus of claim 4, wherein said conducting element comprises an elongate electrically and thermally conductive sheath coaxially surrounding a portion of said cryoprobe with a distal end of said conducting element exposed and a second layer of electrically insulating material covering remainder portions of the conducting element.

6. The apparatus of claim 1, which further comprises a mechanism for providing a cryogenic medium to said cryoprobe.

7. The apparatus of claim 1, wherein said conducting element comprises an elongate sheath disposed over a portion of said cryoprobe, which sheath is removable from said cryoprobe.

8. The apparatus of claim 7, which further comprises a releasable interlock for securing said sheath to said cryoprobe.

9. The apparatus of claim 1, which further comprises a temperature sensor operable to sense the temperature in the region of said cooling portion of said cryoprobe.

10. The apparatus of claim 1, which further comprises a temperature sensor operable to sense the temperature in the region of said second portion.

11. The apparatus of claim 1, wherein said cryoprobe comprises an elongate thermally conductive and electrically conductive needle member into which a cryogenic medium may be passed to produce tissue freezing in the region of the cooling portion.

12. The apparatus of claim 1, wherein said cooling portion and electrically conductive first portion are adjacent the distal end of the cryoprobe.

13. The apparatus of claim 12, wherein said energy conducting element comprises an elongate sheath received on the cryoprobe with the distal end of the cryoprobe extending longitudinally outwardly from said sheath, and said distal end is configured to penetrate tissue.

14. The apparatus of claim 13, wherein said sheath is removably received on said cryoprobe and which further comprises a releasable interlock for securing said sheath to said cryoprobe.

15. The apparatus of claim 13, wherein said electrical insulation is interposed between said cryoprobe and said sheath and a distal end portion of said insulation extends longitudinally outwardly from said sheath and the distal end of said cryoprobe extends longitudinally outwardly from said insulation.

16. Cryosurgical apparatus comprising an elongate cryoprobe having a proximal end and a distal end, said distal end being adapted to be positioned in tissue to be treated and operative to form an ice ball in such tissue upon activation, said distal end having an electrically conductive first portion, an energy conducting element coupled to said cryoprobe and having an electrically conductive second portion in a position spaced toward said proximal end from said first portion, and electrical insulation interposed between said first portion and said second portion, said first and second portions being adapted for operative connection to a source of tissue heating electromagnetic energy to produce heating of tissue in the region of said iceball to control the configuration of the iceball.

17. The apparatus of claim 16, wherein said cryoprobe comprises an elongate electrically conductive member, said energy conducting element surrounds a portion of said conductive member, and said electrical insulation is disposed between said conductive member and said energy conducting element.

18. The apparatus of claim 17, wherein said conducting element comprises an elongate sheath coaxially surrounding a portion of said cryoprobe with a distal end of said conducting element exposed and a second layer of insulating material covering remainder portions of the conducting element.

19. The apparatus of claim 16, wherein said conducting element comprises an elongate sheath disposed over a portion of said cryoprobe, which sheath is removable from said cryoprobe.

20. The apparatus of claim 19, which further comprises a releasable interlock for securing said sheath to said cryoprobe.

21. The apparatus of claim 16, which further comprises a temperature sensor operable to sense the temperature in the region of said distal end of said cryoprobe.

22. The apparatus of claim 16, which further comprises a temperature sensor operable to sense the temperature in the region of said second portion.

23. The apparatus of claim 16, wherein said cryoprobe comprises an elongate thermally and electrically conductive needle member into which a cryogenic medium may be passed to produce tissue freezing in the region of the distal end and a holder is coupled to the proximal end of the cryoprobe.

24. The apparatus of claim 23, wherein said energy conducting element comprises an elongate sheath sized to be received on said needle with the distal end of said needle extending longitudinally outwardly from said sheath.

25. The apparatus of claim 24, which further comprises a releasable interlock for securing said sheath to said cryoprobe.

26. The apparatus of claim 24, wherein said electrical insulation is interposed between said needle and said sheath and a distal end portion of said insulation extends longitudinally outwardly from said sheath and the distal end of said needle extends longitudinally outwardly from said insulation.

27. The apparatus of claim 16, wherein said cryoprobe comprises a connector adapted to be operatively connected to mechanism for providing a cryogenic medium to said cryoprobe.

28. Cryosurgical apparatus comprising an elongate cryoprobe having a proximal end and a distal end, said cryoprobe comprising an elongate needle member into which a cryogenic medium may be introduced, said distal end being adapted to be positioned in tissue to be treated and operative to form an ice ball in such tissue upon activation, said distal end having an exposed electrically conductive first portion, an energy conducting element comprising an elongate sheath coaxially surrounding the cryoprobe with said distal end of the cryoprobe protruding from said sheath, said sheath being removably coupled to said cryoprobe and having an exposed electrically conductive second portion in a position spaced toward said proximal end from said first portion, a first layer of electrical insulation material interposed between said first portion and said second portion, and a second layer of electrical insulation material covering portions of said energy conducting element other than said second portion, said first and second portions being adapted for operative connection to a source of tissue heating energy to direct tissue heating energy through tissue surrounding said iceball to control the configuration of the iceball.

29. The apparatus of claim 28, wherein said first layer of electrical insulation is interposed between said needle and said sheath and a distal end portion of said insulation extends longitudinally outwardly from said sheath and the distal end of said needle extends longitudinally outwardly from said insulation.

30. The apparatus of claim 28, which further comprises a releasable interlock for securing said sheath to said cryoprobe.

31. The apparatus of claim 28, which further comprises a temperature sensor operable to sense the temperature in the region of said distal end of said cryoprobe.

32. The apparatus of claim 28, which further comprises a temperature sensor operable to sense the temperature in the region of said second portion.

33. The apparatus of claim 28, wherein said cryoprobe comprises a connector adapted to be operatively connected to mechanism for providing a cryogenic medium to said cryoprobe.

34. The apparatus of claim 28, wherein said source of energy comprises a radiofrequency energy generator.

35. The apparatus of claim 34, wherein one of said first and second portions is operatively connected to said radiofrequency generator and the other of said first and second portions is connected to electrical ground.

36. A method for controlling the configuration of an iceball formed in tissue by a cryoprobe comprising the steps of providing a cryoprobe having a thermally conductive cooling portion and an electrically conductive first portion, providing an element having electrically conductive second portion surrounding a portion of said cryoprobe in a region spaced from said first portion, and electrical insulation interposed between said first portion and the second portion, inserting the cryoprobe into tissue to be treated, activating the cryoprobe to form an iceball in tissue adjacent the cooling portion, connecting a selected one of said first portion and second portion to a source of tissue heating electromagnetic energy and providing electromagnetic energy to said selected one to produce heating of tissue in the region of said iceball.

37. The method of claim 36, wherein the source of electromagnetic energy is a radiofrequency energy generator.

38. The method of claim 37, which further comprises the step of connecting said selected one to said radiofrequency energy generator and connecting the other to electrical ground.

39. The method of claim 38, which further comprises passing radiofrequency energy from said selected one to the other through tissue surrounding said iceball to heat tissue adjacent the iceball and control the configuration of the iceball.

* * * * *